United States Patent
Tanaka et al.

(10) Patent No.: US 7,105,128 B2
(45) Date of Patent: *Sep. 12, 2006

(54) DRY ANALYTICAL ELEMENT USING WATER-SOLUBLE INDICATOR FOR COLORIMETRY

(75) Inventors: Hideaki Tanaka, Saitama (JP); Yoshihide Iwaki, Saitama (JP); Yoshiki Sakaino, Saitama (JP); Kazuya Kawasaki, Saitama (JP); Yoshikazu Amano, Saitama (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 0 days.

This patent is subject to a terminal disclaimer.

(21) Appl. No.: 10/281,564

(22) Filed: Oct. 28, 2002

(65) Prior Publication Data

US 2003/0138352 A1    Jul. 24, 2003

Related U.S. Application Data

(63) Continuation of application No. 09/512,522, filed on Feb. 24, 2000, now abandoned.

(30) Foreign Application Priority Data

Feb. 24, 1999  (JP) .............................. 1999-046275

(51) Int. Cl.
    *G01N 31/22* (2006.01)

(52) U.S. Cl. .......................................... 422/56; 435/26

(58) Field of Classification Search .................. 422/56, 422/57; 435/4, 15, 26
See application file for complete search history.

(56) References Cited

U.S. PATENT DOCUMENTS

| 5,006,458 | A | * | 4/1991 | Kato et al. ..................... 435/4 |
| 5,037,738 | A | * | 8/1991 | Lamos et al. .................. 435/12 |
| 5,112,740 | A | * | 5/1992 | Nealon et al. ................. 435/15 |
| 5,776,779 | A | * | 7/1998 | Tamura et al. ................. 436/56 |
| 5,801,006 | A | * | 9/1998 | Kaufman ....................... 435/15 |
| 6,068,989 | A | * | 5/2000 | Tanaka et al. ................. 435/26 |
| 6,485,927 | B1 | * | 11/2002 | Tanaka et al. ................. 435/26 |

FOREIGN PATENT DOCUMENTS

WO    WO 9916897    *    4/1999

OTHER PUBLICATIONS

Nealon, D.A. "Reduced Thionicotinamide Adenine Dinucleotide t-NADH; an Alternative to Measuring Dehydrogenase Reactions in the Visible Region" Clinical Chemistry, vol. 37, No. 6 (1991), pp. 915-916.*

* cited by examiner

Primary Examiner—Jeffrey R. Snay
(74) Attorney, Agent, or Firm—Reed Smith LLP

(57) ABSTRACT

This invention relates to a dry analytical element using a water-soluble indicator which improves measuring accuracy, which comprises a water-impermeable support, a water-permeable layer and a spreading layer having a function to spread a liquid uniformly, wherein a water-soluble indicator for colorimetry is incorporated into the spreading layer.

2 Claims, No Drawings

DRY ANALYTICAL ELEMENT USING WATER-SOLUBLE INDICATOR FOR COLORIMETRY

CROSS-REFERENCE TO RELATED APPLICATIONS

This application is a continuation application of U.S. application Ser. No. 09/512,522, filed on Feb. 24, 2000, which is based on Japanese Patent Application No. 046275/1999 filed Feb. 24, 1999. The disclosures of which are incorporated herewith.

BACKGROUND OF THE INVENTION

This invention relates to a dry analytical element for the determination of a substance existing in a liquid sample. The dry analytical element of the invention is particularly useful for the determination of an analyte contained in a biological sample in clinical assay which requires rapid and highly accurate analytical results, such as blood, cerebrospinal fluid, urine or extract of faces.

Recently, dry analytical elements composed of plural layers laminated integrally have been developed as a device for the determination of a small quantity of a liquid sample accurately, and various investigations are being done in order to improve or diversify the dry analytical elements. The dry analytical element contains all reagents for analysis, and can determine only by depositing a drop of liquid sample and measuring a color developed thereon.

Incidentally, indicator compositions used in dry analytical elements are, in general, water-insoluble. The reason is that the dye formed is resistant to diffusion because of being almost insoluble or slightly soluble to water, and as a result, accuracy is improved by the prevention of ringing (Japanese Patent KOKAI 1-320999). On the other hand, selectable reaction systems and indicator compositions for colorimetry are restricted according to the type of analyte, and sometimes, water-soluble indicator compositions must be used. In this case, a special layer for mordanting the water-soluble indicator composition is provided which increases cost and labors.

SUMMARY OF THE INVENTION

An object of the invention is to provide an analytical element having a high accuracy inexpensively, even if the indicator to be used is water-soluble.

The inventors investigated eagerly in order to achieve the above object, and they inadvertently found that, even when an indicator is water-soluble, a high analytical accuracy can be obtained by incorporating the indicator into a spreading layer without mordanting.

The present invention has been completed by the above finding, and accordingly, provides a dry analytical element which comprises a water-impermeable support, a water-permeable layer and a spreading layer having a function to spread a liquid uniformly, wherein a water-soluble indicator for colorimetry is incorporated into the spreading layer.

DETAILED DESCRIPTION OF THE INVENTION

The fundamental layer construction of the dry analytical element of the invention is composed of a water-impermeable light-transmissive support, a water-permeable layer and a porous spreading layer laminated in this order.

The porous spreading layer has a function to spread the components contained in an aqueous sample in plane substantially without unevenness, and to supply the aqueous sample to the water-permiable layer beneath at almost a constant rate per unit area, and every known spreading layer used in dry analytical elements can be used irrespective of fibrous or non-fibrous material. Illustrative of the spreading layers are nonfibrous isotropic porous medium layers represented by a membrane filter (blushed polymer layer) disclosed in U.S. Pat. No. 3,992,158, nonfibrous porous layers represented by a continuous microspace-containing three-dimensional lattice granular structure layer where polymer particulates are joined so as to contact with each other at a point by using an adhesive which is not swell in water disclosed in Japanese Patent KOKAI 55-90859, porous layers made of woven fabric disclosed in U.S. Pat. Nos. 4,292,272, 4,783,315, etc., knitted fabric layers disclosed in EP 0 162 302A, etc., and the like.

Other examples of the spreading layer are porous membranes made of cellulose derivative, such as cellulose diacetate, cellulose triacetate, nitrocellulose, hydroxymethyl cellulose, or hydroxyethyl cellulose, porous membranes made of olefin polymer or copolymer, such as polyethylene, polypropylene, polystyrene or polyvinyl chloride, porous membranes made of polyethylene terephthalate, polycarbonate or polysulfone, porous membranes made of a plymer or copoymer of acrylic acid, methacrylic acid or their esters, porous membranes of condensation polymer, such as nylon, polyamide or polyurethane, porous membranes made of inorganic particulates, such as glass particulates or diatomaceous earth joined by a small amount of polymer, porous membranes made of polytetrafluoroethylene, filter paper, glass fiber filter, and the like.

Two or more spreading layers may be incorporated. For example, two or more porous layers which are joined by an adhesive disposed in spots, such as disclosed in Japanese Patent KOKAI 61-4959, 62-138756, 62-135757 or 62-138758.

In order to accelate spreading of sample, a nonionic, anionic, cationic or ampholytic surfactant may be incorporated into the spreading layer.

A spreading controller, such as a hydrophilic polymer may be incorporated into the spreading layer in order to control spreading ability. Various reagents or a part of reagent(s) may also be incorporated for the purpose of accelerating object detecting reaction or reducing or inhibiting interfering reaction(s).

A suitable thickness of the spreading layer is 20 to 200 μm, preferably 50 to 170 μm, more preferably 80 to 150 μm.

A representative water-permeable layer is a hydrophilic polymer layer. The hydrophilic polymer layer usually contains at least a part of reagent(s) necessary for analysis, and in this case, the layer is called reagent layer. Hydrophilic polymers usable for the layer include various water-soluble or swellable and hydrophilic polymers used in known dry analytical elements which have a swelling ratio in the range of about 1.5 to about 20, preferably from about 2.5 to about 15 at a water absorption at 30° C. Illustrative of the hydrophilic polymer are gelatins, such as acid-treated gelatin and deionized gelatin, gelatin derivatives, such as phthalated gelatin and hydroxyacrylate-graft gelatin, agarose, pullulan, pullulan derivatives, polyacrylamide, polyvinyl alcohol and polyvinylpyrrolidone.

Instead of the hydrophilic polymer layer, a porous polymer membrane can be used.

A suitable dry thickness of the reagent layer is about 1 μm to about 100 μm, preferably about 3 μm to about 50 μm, more preferably about 5 μm to about 30 μm. The reagent layer is preferably transparent.

Various reagents or a part of reagent(s) may also be incorporated into the hydrophilic polymer layer for the purpose of accelerating object detecting reaction or reducing or inhibiting interfering reaction(s).

A suitable support is a water-impermeable light-transmissive support used for a conventional known dry analytical element, and includes a transparent film or sheet made of polyethylene terephthalate, polycarbonate of bisphenol A, polystyrene, cellulose ester, such as cellulose diacetate, cellulose triacetate and cellulose acetate propionate, or the like. The thickness of the support is usually in the range of about 50 μm to about 1 mm, preferably from about 80 μm to about 300 μm. The support may be provided with an undercoating layer or an adhesive layer on its surface in order to strengthen the adhesion of the reagent layer laminated thereon. Instead of the undercoating layer, the surface of the support may be treated by a physical activation, such as, glow discharge or corona discharge or by a chemical activation.

Various layers may further be incorporated into the dry analytical element according to analytical item and the like. Examples of the layers are registration layer, water absorption layer, light-reflecting layer, light-blocking layer, and so on.

The analyte to be measured by the dry analytical element of the invention is not especially limited, and includes enzymes, lipids, inorganic ions, metabolites, proteins, various globlins, antigens, antibodies, drugs, hormones, tumor-markers, DNA, RNA and the like.

The dry analytical element of the invention contains all reagent(s) necessary for analysis, and the all reagent(s) may be the same as those of known dry analytical element except for the indicator for colorimetry. The all reagent(s) necessary for analysis are indispensable ones, and the other reagents may be added or deleted.

The indicator for colorimetry includes chromogens and coloring substrates which are colored or colorless. The chromogens and coloring substrates produce a determinable color change directly or indirectly which is measurable quantitatively. The chromogen may be dye, dye former or dye precursor. The indicator used in the invention is water-soluble, and has a solubility in water of 0.1% by weight or more, usually 0.5% by weight or more. Illustrative of the indicators are diazonium salts, such as dichlorobenzene diazonium and benzenesulfonic acid diazonium, colorimetry reagents, such as Alfusone and azomethine H, reduction type coloring agents, such as WST-1 and WST-3, coloring substrates, such as p-nitrophenyl derivatives, aminoaniline derivatives, 3-indole derivatives, p-nitroaniline derivatives and thio-NADH, pH indicators, such as Methyl Violet 6B, m-Cresol Purple, Congo Red, Methyl Orange, tetrabromophenol Blue, sodium alizarinsulfonate, litmus, Bromophenol Red, Thymol Blue, Nile Blue and p-nitrohenol, metal indicators, such as Anisidine Blue, Arsenazo-III, Bathocuproine disulfonic acid, disodium salt, Bathophenanthroline disulfonic acid, disodium salt, Eriochrome Black T, Calcichrome, Calmagite, Carboxyarsenazo, Chlorophosphonazo-III, Chrome Azurol S, Dimethylsulfonazo-III, Dinitrosulfonazo-III, Methylthymol Blue, Methylxylenol Blue, Neo-Thorin, Sulfonazo-III, Xylidyl Blue-I, Xylidyl Blue-II, Nitro-PAPS, Phthalein Complexone, PDTS, Pyrocatechol Violet and Zylenol Orange, oxidation type coloring agents, such as DAB, HPPA, TMBZ.HCl, DA-67, DA-64, ABTS, MCDP, BCMA and LLGB, couplers, such as 4-aminoantipyrine, Trinder reagents, such as ADPS, ALPS, DAPS, HADAPS, MAPS, TOPS, ADOS, ALOS, DAOS, HDAOS, MAOS, TOOS, and HALPS, and the like.

A representative dry analytical element to which the present invention is applied is a dry analytical element for the determination of bicarbonate ion.

The reagent system employed for the dry analytical element uses phosphoenolpyruvate carboxylase and malate dehydrogenase, wherein thioNAD(P)H and NAD(P)H are used as substrates of malate dehydrogenase.

In the above reaction system, reaction proceeds as follows:

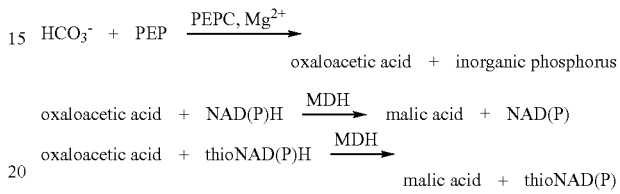

Since thioNAD(P)H has an absorption peak at 400 nm, a visible light source and detection system can be used. In the case of thioNAD(P)H alone, since the absorbance is high, the determination range becomes narrow. However, this phenomenon can be avoided by combining NAD(P)H at a prescribed ratio. Although it is uncertain how competitive reaction proceeds between thioNAD(P)H and NAD(P)H, as a result of measuring as to samples containing bicarbonate ion in various concentration, surprisingly, it was found that bicarbonate ion can be determined in a wide range with good reproducibility.

Phosphoenolpyruvate carboxylase applicable to the invention functions to produce oxaloacetic acid from phosphoenolpyruvic acid, and includes EC4.1.1.31, EC4.1.1.32, EC4.1.1.38 and EC4.1.1.49. However, the presence of GDP is necessary for EC 4.1.1.32, inorganic phosphorus is necessary for EC 4.1.1.38, and ADP is necessary for EC 4.1.1.49, respectively.

As malate dehydrogenase, there are EC 1.1.1.37, EC 1.1.1.38, EC 1.1.1.39, EC 1.1.1.40, EC 1.1.1.83 and EC 1.1.99.16. The malate dehydrogenase applicable to the invention functions to produce malic acid from oxaloacetic acid, and includes EC 1.1.1.37 and EC 1.1.99.16.

The measuring reagent composition for the determination of bicarbonate ion also contains substrates of the above coupled enzymes. The substrate of phosphoenolpyruvate carboxylase includes phosphoenolpyruvic acid and derivatives thereof on which the enzyme can act. The substrate of malate dehydrogenase used in the invention is a combination of thioNADH (thionicotinamide adenine dinucleotide) in reduced form or thioNADPH (thionicotinamide adenine dinucleotide phosphate) in reduced form and NADH (nicotinamide adenine dinucleotide) in reduced form or NADPH (nicotinamide adenine dinucleotide phosphate). ThioNAD(P)H is the same as NAD(P)H except that —$CONH_2$ in nicotinamide group is changed to —$CSNH_2$. ThioNAD(P)H is commerically available, and for example, sold by Sigma Chemical Co. A suitable molar ratio of thioNAD(P)H/NAD(P)H is 1/0.05–1/2, preferably 1/0.1–1/1, more preferably 1/0.2–1/0.7.

In the case of determining the bicarbonate ion concentration of a blood sample, it is preferable to incorporate carbonic anhydrase inhibitor into the reagent system. Applicable carbonic anhydrase inhibitors are acetazolamide, derivatives thereof, benzenesulfonamide, derivatives thereof and the like, and benzenesulfonamide and derivatives thereof found by the inventors are preferred. The derivatives of benzenesulfonamide have benzenesulfonamide structure of which one or two hydrogen atoms of the benzene ring were substituted. Illustrative of the substituents are hydroxyl group, amino group, halogen (fluorine, chlorine, bromine, iodine) atoms, nitro group, amide group, sulfonic group, carboxyl group, sulfonamide group, methyl group, ethyl group, propyl group, aminomethyl group, aminoethyl group, aminopropyl group, hydroxymethyl group, hydroxyethyl group, hydroxypropyl group, phosphate group, methoxy group, ethoxy group, and the like. Preferable substituents are amino group, halogen atoms, sulfonamide group, methyl group, aminoethyl group and the like. Examples of preferable benzenesulfonamide derivatives are p-toluenesulfonamide, 1-chlorobenzene-2,4-disulfonamide, 4-(2-aminoethyl) benzenesulfonamide, and the like, and p-toluenesulfonamide and 4-(2-aminoethyl) benzenesulfonamide are particularly preferable because of having excellent safety against skin and eye.

The measuring reagent composition may contain other components, such as known enzyme activators (e.g. $Mg^{2+}$), stabilizer, pH buffer (e.g. trishydroxymethylaminomethane), and the like.

A suitable amount of phosphoenolpyruvic acid is about 1.5 to 10 moles, preferably about 2 to 5 moles per 1 mole bicarbonate ion.

A suitable amount of the sum of thioNAD(P)H and NAD(P)H is about 1 to 10 moles, preferably about 1.5 to 5 moles per one mole of $HCO_3^-$. A suitable ratio of phosphoenopyruvate carboxylase/malate dehydrogenase is about 1 to 1/20, preferably about 1 to 1/10.

A suitable amount of carbonic anhydrase inhibitor is about 5 to 2,000 $mg/m^2$, preferably about 50 to 1,000 $mg/m^2$. When the content is too great, deposition occurs.

EXAMPLES

Example 1

This example is a model of the present invention, and illustrates by using only a water-soluble dye without adding reagent composition participating with detection reaction.

An aqueous solution containing the following reagents was applied onto a clear PET base 180 μm in thickness so as to become the following coating amount, and dried.

| | |
|---|---|
| Gelatin | 13.0 $g/m^2$ |
| Tricine | 3.0 $g/m^2$ |
| Nonionic surfactant | 0.25 $g/m^2$ |

A knitted fabric made of polyester was laminated as the spreading layer thereto, and an aqueous solution containing the following reagents was applied thereonto so as to become the following coating amount in order to control spreading of sample, followed by drying.

| | |
|---|---|
| Nonionic surfactant | 1.0 $g/m^2$ |
| Polyvinylpyrolidone | 2.5 $g/m^2$ |
| Methylene Blue | 0.03 $g/m^2$ |

The laminate was cut into pieces of about 1.2×1.3 cm, and integrated into a mount having an opening 10 mm in diameter to prepare analytical elements, 10 μl water drop was deposited onto the analytical element, and incubated at 37° C. for 6 minutes. Reflection optical density of the dry analytical element was measured at 650 nm, and reproducibily of n=20 was shown in Table 1.

Comparative Example 1

Dry analytical elements were prepared similar to Example 1, except that Methylene Blue was not incorporated into the spreading layer but into the gelatin layer.

10 μl water drop was deposited onto the analytical element, and incubated at 37° C. for 6 minutes. Reflection optical density of the dry analytical element was measured at 650 nm, and reproducibily of n=20 was shown in Table 1.

TABLE 1

| | 6 mm $\overline{OD}$ (n = 20) | SD (n = 20) | CV (n = 20) |
|---|---|---|---|
| Example 1 | 0.712 | 0.003 | 0.4% |
| Comparative 1 | 0.990 | 0.011 | 1.1% |

It can be seen from the data of Table 1 that analytical accuracy is improved by imcorporating water-soluble dye not into the hydrophilic polymer layer but into the spreading layer.

Example 2

This example illustrates the present invention applied to a dry analytical element for the determination of total bicarbonate ions in a liquid.

An aqueous solution containing the following reagents was applied onto a clear PET base 180 μm in thickness so as to become the following coating amount, and dried.

| | |
|---|---|
| Nonionic surfactant | 0.25 $g/m^2$ |
| Magnesium chloride | 1.9 $g/m^2$ |
| Gelatin | 13.0 $g/m^2$ |
| Tricine | 3.0 $g/m^2$ (pH 8.0) |
| MDH (EC 4.1.1.31) | 24 $KU/m^2$ |
| PEPC (EC 1.1.1.37) | 2.4 $KU/m^2$ |

An aqueous solution containing the following reagents was applied onto the above layer so as to become the following coating amount, and dried.

| | |
|---|---|
| Nonionic surfactant | 0.25 $g/m^2$ |
| Gelatin | 6.0 $g/m^2$ |
| Tricine | 1.0 $g/m^2$ (pH 8.0) |
| Titanium dioxide | 5.4 $g/m^2$ |

A knitted fabric made of polyester was laminated as the spreading layer thereto, and an aqueous solution containing the following reagents was applied thereonto so as to become the following coating amount in order to control spreading of sample, followed by drying.

| | |
|---|---|
| Nonionic surfactant | 0.25 $g/m^2$ |
| Tricine | 3.0 $g/m^2$ (pH 8.0) |

-continued

| | |
|---|---|
| PEP | 2.0 g/m² |
| NADH | 1.5 g/m² |
| ThioNADH | 2.2 g/m² |
| Polyvinylpyrrolidone | 3.0 g/m² |

The laminate was cut into pieces of about 1.2×1.3 cm, and integrated into a mount having an opening 10 mm in diameter to prepare analytical elements, 10 μl 10 mM, 25 mM or 35 mM bicarbonate solution drop was deposited onto the analytical element, and incubated at 37° C. for 6 minutes. Reflection optical density of the dry analytical element was measured at 425 nm, and reproducibility of n=20 was shown in Table 2.

Comparative Example 2

Dry analytical elements were prepared similar to Example 2, except that thio NADH and NADH were not incorporated into the spreading layer but into the gelatin layer.

10 μl 10 mM, 25 mM or 35 mM bicarbonate solution drop was deposited onto the analytical element, and incubated at 37° C. for 6 minutes. Reflection optical density of the dry analytical element was measured at 425 nm, and reproducibility of n=20 was shown in Table 2.

TABLE 2

| | | 6 min $\overline{OD}$ (n = 20) | SD (n = 20) | CV (n = 20) |
|---|---|---|---|---|
| Example 2 | 10 mM | 1.418 | 0.008 | 0.59% |
| | 25 mM | 1.114 | 0.011 | 1.02% |
| | 35 mM | 0.847 | 0.008 | 1.00% |
| Comparative 2 | 10 mM | 1.313 | 0.031 | 2.38% |
| | 25 mM | 0.816 | 0.038 | 4.70% |
| | 35 mM | 0.563 | 0.027 | 4.80% |

It can be seen from the data of Table 2 that analytical accuracy is improved by imcorporating water-soluble dye (thioNADH and NADH) not into the hydrophilic polymer layer but into the spreading layer.

The invention claimed is:

1. A dry analytical element which comprises a water-impermeable support, a water-permeable layer and a spreading layer having a function to spread a liquid uniformly and which contains phosphoenolpyruvate carboxylase and malate dehydrogenase, wherein a water-soluble indicator for colorimetry is incorporated into the spreading layer, the water-soluble indicator is a combination of thioNAD(P)H and NAD(P)H and the dry analytical element is for the measurement of bicarbonate ion.

2. A dry analytical element for the measurement of bicarbonate ion using phosphoenolpyruvate carboxylase and malate dehydrogenase, which comprises in this order, a water-impermeable support, a water-permeable layer and a spreading layer which contains a water-soluble indicator for colorimetry comprising a combination of thioNAD(P)H and NAD(P)H.

* * * * *